(12) United States Patent
Aimiya et al.

(10) Patent No.: US 8,513,031 B2
(45) Date of Patent: Aug. 20, 2013

(54) FLUORESCENT SUBSTANCE-CONTAINING SILICA NANOPARTICLES WITH COATING HAVING HIGH BULK REFRACTIVE INDEX

(75) Inventors: Takuji Aimiya, Tokyo (JP); Hideki Hoshino, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 0 days.

(21) Appl. No.: 13/517,271

(22) PCT Filed: Nov. 4, 2010

(86) PCT No.: PCT/JP2010/069574
§ 371 (c)(1),
(2), (4) Date: Jun. 20, 2012

(87) PCT Pub. No.: WO2011/077838
PCT Pub. Date: Jun. 30, 2011

(65) Prior Publication Data
US 2012/0252140 A1    Oct. 4, 2012

(30) Foreign Application Priority Data

Dec. 25, 2009   (JP) ................................. 2009-294194

(51) Int. Cl.
*G01N 33/552* (2006.01)
*G01N 33/553* (2006.01)

(52) U.S. Cl.
USPC ............ 436/525; 436/527; 977/773; 977/774

(58) Field of Classification Search
USPC .......................... 436/525, 527; 977/773, 774
See application file for complete search history.

(56) References Cited

U.S. PATENT DOCUMENTS

| | | | | |
|---|---|---|---|---|
| 5,990,479 A | * | 11/1999 | Weiss et al. | 850/56 |
| 6,548,264 B1 | * | 4/2003 | Tan et al. | 435/7.21 |
| 6,699,724 B1 | * | 3/2004 | West et al. | 436/525 |
| 7,122,384 B2 | * | 10/2006 | Prober et al. | 436/524 |
| 7,368,086 B2 | * | 5/2008 | Naasani | 422/82.08 |
| 7,842,505 B2 | * | 11/2010 | Noda et al. | 436/56 |
| 8,080,430 B2 | * | 12/2011 | Imamura et al. | 436/525 |
| 2002/0132371 A1 | * | 9/2002 | Kreimer et al. | 436/525 |
| 2004/0101822 A1 | * | 5/2004 | Wiesner et al. | 435/5 |
| 2005/0281884 A1 | * | 12/2005 | Adair et al. | 424/489 |
| 2007/0155021 A1 | * | 7/2007 | Zhang et al. | 436/518 |
| 2010/0047859 A1 | * | 2/2010 | Lee | 435/40.5 |
| 2011/0256528 A1 | * | 10/2011 | Poetter et al. | 435/5 |
| 2011/0263037 A1 | * | 10/2011 | Herz et al. | 436/163 |
| 2013/0029428 A1 | * | 1/2013 | Kim et al. | 436/501 |
| 2013/0108552 A1 | * | 5/2013 | Sharma et al. | 424/9.32 |

FOREIGN PATENT DOCUMENTS

| | | |
|---|---|---|
| JP | 2003-321226 | 11/2003 |
| JP | 2009-530497 | 8/2009 |
| JP | 2009-196829 | 9/2009 |
| WO | 2007/074722 | 7/2007 |
| WO | WO 2009/116408 * | 9/2009 |

OTHER PUBLICATIONS

Mulder et al. "Size-selective detection in integrated optical interferometic biosensors", Optics Express (2012). 20(19):20934-20950.*

* cited by examiner

*Primary Examiner* — Shafiqul Haq
*Assistant Examiner* — Gary E Hollinden
(74) *Attorney, Agent, or Firm* — Lucas & Mercanti, LLP

(57) ABSTRACT

Disclosed are fluorescent substance-containing silica nanoparticles containing a fluorescent substance therein featured in that the surface of the silica nanoparticles is coated with a material having a bulk refractive index of from 1.60 to 4.00. The invention can provide fluorescent substance-containing silica nanoparticles excellent in long term storage stability and a biosubstance labeling agent employing the same.

6 Claims, No Drawings

FLUORESCENT SUBSTANCE-CONTAINING SILICA NANOPARTICLES WITH COATING HAVING HIGH BULK REFRACTIVE INDEX

CROSS REFERENCE TO RELATED APPLICATION

This Application is a 371 of PCT/JP2010/069574 filed on Nov. 4, 2010 which, in turn, claimed the priority of Japanese Patent Application No 2009-294194 filed on Dec. 25, 2009, both applications are incorporated by reference herein.

FIELD OF THE INVENTION

The present invention relates to fluorescent substance-containing silica nanoparticles and a biosubstance labeling agent employing the same.

TECHNICAL BACKGROUND

In order to diagnose disease or the conditions of disease, detection of a specific biomolecule (biomarker) contained in blood and the like has been noted.

Presently, in order to detect the biomolecule, immunoassay employing an antigen-antibody reaction is mainly employed. A chemical luminescence method employing an enzyme reaction is presently prevailing on account of high sensitivity. However, the use of the enzyme, which is a biosubstance, requires complicated operations such as severe temperature control and the like. More simple systems are desired.

As one of the methods, there is known a fluorescence immunoassay method employing a biosubstance labeling agent labeled in advance with a fluorescent substance. As the fluorescent substance, an organic dye or a quantum dot can be used. The fluorescence immunoassay method can be carried out more simply as compared with the chemical luminescence method. However, the fluorescence intensity of the fluorescent substance used is extremely low, resulting in poor detection sensitivity.

Recently, in order to diagnose disease in an extremely early stage, i.e., to carry out detection of an extremely small amount of a biomarker, a biosubstance labeling agent labeled with a fluoresce substance emitting fluorescence with high density is demanded. As one method for obtaining such a substance, there is a method which incorporates a fluorescent substance in one silica nanoparticle (see, for example, Patent Documents 1 and 2).

Patent Document 3 discloses that fluorescent dye-containing silica particles are coated with silica in order to increase the emission luminance. Patent Document 4 discloses that silica particles containing a fluorescent dye in the connecting pores are coated with silica.

The present inventors prepared fluorescent dye-containing silica particles coated with silica according to the method as disclosed in Patent Document 3, and carried out fluorescence immunoassay after one month's storage. As a result, a ratio (S/N ratio) of the fluorescence intensity S due to the labeling agent combined with a biomarker to be detected to the fluorescence intensity N due to the labeling agent in the absence of a biomarker to be detected proved to be small.

The present inventors also prepared a quantum dot-containing silica prepared according to a method disclosed in Patent document 2, and prepared a quantum dot-containing silica with a silica coating according to a method disclosed in Patent document 3, Both quantum dot-containing silicas showed the result similar to that described above.

The above result means that when the fluorescent substance-containing silica prepared according to a known technique is applied to extracorporeal diagnosis medicines, there is problem in long term storage stability. Further improvement is desired.

Prior Art Document
Patent Document
Patent Document 1: WO 07/074722
Patent Document 2: Japanese Patent O.P.I. Publication No. 2003-321226
Patent Document 3: Japanese Unexamined Patent Application Publication (Translation of PCT Application) No. 2006-514708
Patent Document 4: Japanese Patent O.P.I. Publication No. 2009-196829

DISCLOSURE OF THE INVENTION

Problems to be Solved by the Invention

The present invention has been made in view of the above. An object of the invention is to provide fluorescent substance-containing silica nanoparticles which excel in long-term storage stability and a biosubstance labeling agent employing the same.

Means for Solving the Problems

The above object of the invention can be attained by the following constitutions.

1. Fluorescent substance-containing silica nanoparticles containing a fluorescent substance in silica particles, featured in that the surface of the silica nanoparticles is coated with a material having a bulk refractive index of from 1.60 to 4.00.
2. The fluorescent substance-containing silica nanoparticles as described in item 1 above, featured in that the material having a bulk refractive index of from 1.60 to 4.00 is a material having a bulk refractive index of from 1.76 to 2.58.
3. The fluorescent substance-containing silica nanoparticles as described in item 2 above, featured in that the material having a bulk refractive index of from 1.76 to 2.58 is at least one selected from titanium oxide, zirconium oxide and aluminum oxide.
4. The fluorescent substance-containing silica nanoparticles as described in any one of items 1 to 3 above, featured in that the fluorescent substance is an organic dye.
5. The fluorescent substance-containing silica nanoparticles as described in any one of items 1 to 3 above, featured in that the fluorescent substance is a quantum dot.
6. A biosubstance labeling agent comprising a molecule labeling agent featured in that the molecule labeling agent combines with the fluorescent substance-containing silica nanoparticles as described in any one of items 1 to 5 above through an organic molecule.

Effects of the Invention

The present invention can provide fluorescent substance-containing silica nanoparticles which excel in long-term storage stability, and a biosubstance labeling agent employing the same.

PREFERRED EMBODIMENTS FOR CARRYING OUT THE INVENTION

Next, a preferred embodiment for carrying out the invention will be explained in detail.

The present inventors have made an extensive study in order to solve the above problems, and as a result, they have found that the fluorescent substance-containing silica nanoparticles, the surface of which is coated with a material having a bulk refractive index of from 1-60 to 4.00, significantly prevent an S/N ratio obtained according to fluorescence immunoassay from lowering, resulting in detection with high sensitivity. It has been found that in the fluorescent substance-containing silica nanoparticles coated with silica, obtained according to a conventional method, the fluorescent substance contained in the nanoparticies gradually leaks out, and when fluorescence immunoassay is carried out after long term storage of the nanoparticles, fluorescence intensity at a portion to be detected lowers and noise at the background increases, resulting in reduction of the S/N ratio.

In the invention, although details are not clear, it is considered that since the material having a bulk refractive index of from 1.60 to 4.00 used in the coating of the particles has a high density, it prevents the fluorescent substance from physically diffusing and leaking out.

That is, the present inventors have found that the fluorescent substance-containing silica nanoparticles coated with a material having a bulk refractive index of from 1.60 to 4.00 and the biosubstance labeling agent employing the same can be obtained, and completed the invention.

The fluorescent substance-containing silica nanoparticles of the invention are featured in that in the fluorescent substance-containing silica nanoparticies containing a fluorescent substance, the surface of the silica nanoparticies is coated with a material having a bulk refractive index of from 1.60 to 4.00. This is technical feature common in the invention as described herein.

As the preferred embodiment of the invention, the material having a bulk refractive index of from 1.60 to 4.00 is at least one selected from titanium oxide, zirconium oxide and aluminum oxide, from the viewpoint that the advantage of the invention is effectively exhibited.

It is preferred that the fluorescent substance be an organic dye. Further, it is also preferred that the fluorescent substance is a quantum dot.

The fluorescent substance-containing silica nanoparticles of the invention can be suitably used in a biosubstance labeling agent obtained by combining the fluorescent substance-containing silica nanoparticles with a molecule labeling agent through an organic molecule.

Next, the present invention, the constitutions and the preferred embodiment for carrying out the invention will be explained in detail.

[Manufacturing Method of Silica Nanoparticles]

It is preferred that the silica nanoparticles are manufactured according to a method called a Stober method described, for example in Journal of Colloid Science, Vol. 26, page 62 (1968) in which hydrolysis of a silicon-containing alkoxide compound such as tetraethoxysilane and the like is carried out under alkaline condition using aqueous ammonia. The particle diameter can be freely adjusted employing known reaction conditions such as an amount to be added of water, ethanol or alkali, so that silica nanoparticles with an average particle diameter of 30 to about 800 nm can be obtained. Further, with respect to a coefficient of variation showing variation of particle diameters, silica nanoparticles with a coefficient of variation of 20% or less can be obtained.

In the invention, the average particle diameter implies the average of the diameters of circles having the same areas as the sectional areas of a large number of particles, the sectional areas being measured employing an electron micrograph of the particles being taken through a scanning electron microscope (SEM). In the invention, the average particle diameter is an arithmetic average of the diameters of 1000 particles. The coefficient of variation is one determined from a particle diameter distribution with respect to 1000 particles.

[Manufacturing Method of Fluorescent Dye-Containing Silica Nanoparticles and Manufacturing Method of Biosubstance Labeling Agent]

With respect to a manufacturing method of the fluorescent substance containing silica nanoparticles, reference is made to a known method, for example, a method described in a non-patent literature Langmuir Vol. 8, p. 2921 (1992).

Step (1):
A silicon-containing alkoxide compound such as tetraethoxysilane and a fluorescent substance are mixed.

Step (2):
An organic solvent such as ethanol, water and a base are mixed.

Step (3):
The fluorescent substance-containing solution prepared at the Step (1) is added to the mixed solution prepared at the Step (2) while stirring, whereby reaction proceeds.

Step (4):
Fluorescent dye-containing silica nanoparticles produced in the resulting reaction mixture are collected by filtration or centrifugation.

Step (5):
A precursor giving a material having a refractive index of from 1.60 to 4.00 is added to a dispersion solution of the fluorescent dye-containing silica nanoparticles obtained at the Step (4), and reacted so that coating of the nanoparticles proceeds.

Step (6):
Thus, the fluorescent substance-containing silica nanoparticles coated with a material with a refractive index of from 1.60 to 4.00 obtained at the Step (5) are combined with a molecule labeling agent to obtain a biosubstance labeling agent.

As the silicon-containing alkoxide compound used at the Step (1), there are mentioned a tetraalkoxysilane such as tetraethoxysilane or tetramethoxysilane and a trialkoxysilane such as methyltrimethoxysilane, methylethoxysilane or phenyltrimethoxysilane. Further, a silicon-containing alkoxide compound having an organic functional group is mentioned. Typical examples thereof include mercaptopropyltriethoxysilane and aminopropyltriethoxysilane.

The silicon-containing alkoxide compounds described above may be used alone or as an admixture of two or more kinds thereof.

The fluorescent substance used in the fluorescent substance-containing silica nanoparticles in the invention is preferably a substance which emits a visible to near-infrared light with a wavelength range of from 400 to 900 nm when excited with an ultraviolet to near-infrared light with a wavelength range of from 200 to 700 nm.

As a fluorescent substance, an organic dye can be used. As the organic dye, there are mentioned a rhodamine based dye molecule, Alexa Fluor (produced by Invitrogen Corporation) based dye molecule, BODIPY (produced by Invitrogen Corporation) based dye molecule, a cascade based dye molecule, a coumarin based dye molecule, an eosin based dye molecule, an NBD based dye molecule, a pyrene based dye molecule, a Texas red based dye molecule, and a cyanine based dye molecule.

Typical examples thereof include 5-carboxyfluorescein, 6-carboxyfluorescen, 5,6-dicarboxyfluorescein, 6-carboxy-2',4,4',5',7,7'-hexachlorofluorescein, 6-carboxy-2',4,7,7'-tetrachlorofluorescein, 6-carboxy-4',5'-dichloro-2',7'- dimethoxyfluorescein, naphthofluorescein, 5-carboxyrhodamine, 6-carboxyrhodamine, 5,6-dicarboxyrhodamine, Rhodamine 6G, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY 493/503, BODIPY 530/550, BODIPY 558/568, BODIPY 564/570, BODIPY 576/589, BODIPY 581/591, BODIPY 630/650, BODIPY 650/665 (each produced by Invitrogen Corporation), methoxycoumarin, eosin, NBD, pyrene, Cy5, Cy5.5 and Cy7.

The dyes described above may be used as carboxylic acid derivatives or active ester derivatives. In this case, the carboxylic acid group or the active ester group can be reacted with a silicon-containing alkoxide compound having an amino group, for example, aminopropyltriethoxysilane.

As the fluorescent substance, there is a quantum dot.

The quantum dot in the invention implies a semiconductor crystal particle having a particle diameter of 100 nm or less which has a specific emission property derived from quantum confinement effect. The quantum dot has a particle diameter of ordinarily from 2 nm to about 10 nm, and an emission wave length thereof can be controlled by varying the particle diameter.

As the quantum dot, any one of the quantum dots containing as a component, compounds belonging to groups II-VI represented by CdSe, CdS and CdTe, compounds belonging to groups III-V represented by InP, InN, InAs, InGaP, GaP and GaAs, or elements belonging to group IV represented by Si and Ge (referred to also as "II-VI group quantum dots", "III-V group quantum dots" and "IV group quantum dots", respectively) can be used.

As typical examples of CdSe, there are mentioned Qdot 525, Qdot 565, Qdot 585, Qdot 605, Qdot 625, and Qdot 655 (each produced by Invitrogen Corporation); and eFluor $490^{NC}$, eFluor $525^{NC}$, eFluor $605^{NC}$, eFluor $625^{NC}$ (each produced by Novel Science Co., Ltd.). As typical examples of InGaP, there is mentioned eFluor $700^{NC}$ (produced by Novel Science Co., Ltd.).

Each quantum dot described above may be subjected to surface treatment as necessary, employing an organic polymer and the like. As a surface modification group, there is mentioned, for example, an amino group, a carboxyl group, a polyethylene glycol group, a peptide group, a biotin group or a streptavidin group.

The mixed ratio of the silicon-containing alkoxide compound to the fluorescent substance is not limited, but it is preferred that the fluorescent substance is incorporated in the silica nanoparticles finally obtained in an amount of from $1 \times 10^{-6}$ mol/l to $1 \times 10^{-2}$ mol/l, in order to obtain sufficient fluorescence, and prevent concentration quenching.

The solvent used at the Step (2) may be one used in a conventional hydrolysis reaction of the silicon-containing alkoxide compound, and as such a solvent, methanol, ethanol, tetrahydrofuran, dimethylformamide and dimethylsulfoxide are used. These may be used alone or as an admixture of two or more kinds thereof.

The base used at the Step (2) may be one used in a conventional hydrolysis reaction of the silicon-containing alkoxide compound. As such a base, ammonia, sodium hydroxide, and potassium hydroxide can be used and they may be dissolved in water and used as an aqueous solution thereof.

When tetraethoxysilane is used as the silicon-containing alkoxide compound, ethanol is used as the organic solvent, and aqueous ammonia is used as the base, the used amount thereof is as follows, When 1 mol of tetraethoxysilane, a mol of ethanol, r mol of water, and b mol of ammonia are mixed, a is from 20 to 400, r is from 10 to 200, and h is from 10 to 40. Specifically, reference can be made to the conditions described in Journal of Colloid Science Vol. 26, p. 62 (1968).

The reaction temperature at the Step (3) may be one applied in a conventional hydrolysis reaction of the silicon-containing alkoxide compound, and the reaction can be carried out at from room temperature to 50° C.

A method to add the fluorescent dye containing solution is not specifically limited, and can be carried out employing a syringe pump or a dropping funnel.

The reaction time at the Step (3) may be one applied in a conventional hydrolysis reaction of the silicon-containing alkoxide compound, and the reaction time is preferably from one to 50 hours in view of yield and prevention of insoluble matter occurrence.

As a method to collect fluorescent substance-containing silica nanoparticles produced in the reaction mixture at the Step (4), a filtration or centrifugation method can be used which is carried out in a conventional nanoparticle collection method. The collected fluorescent substance-containing silica nanoparticles may be optionally washed with water or an organic solvent, in order to eliminate unreacted materials and the like.

(Coating with Material with Bulk Refractive Index of 1.60 to 4.00)

The fluorescent substance-containing silica nanoparticles in the invention are coated with a material having a bulk refractive index of from 1.60 to 4.00. An inorganic material having a bulk refractive index of less than 1.60 does not give the effect of the invention probably due to its low density. An inorganic material having a bulk refractive index of more than 4.00 increases the refraction of fluorescence emitted from the fluorescent substance contained in the nanoparticles, which makes it difficult to gather light in a light detection device. It is preferred that the nanoparticles are coated with a material having a bulk refractive index of from 1.60 to 3.00.

The bulk refractive index in the invention refers to an absolute refractive index, the refractive index of a vacuum being assigned at a value of 1, and to a value measured through an Abbe's refractometer.

Specifically as the refractive indeces, the values described in for example, "Kagaku Daijiten", published by Kyoritsu Shuppan (1960) can be applied.

As a material having a bulk refractive index of from 1.60 to 4.00, metal oxides, metal sulfates and metal sulfides are preferred. Examples thereof include aluminum oxide (α alumina) (with a refractive index of 1.76), zirconium oxide (with a refractive index of 2.20), titanium dioxide (with a refractive index of 2.58), barium sulfate (with a refractive index of 1.64) and zinc sulfide (with a refractive index of 2.37).

Among these, aluminum oxide, titanium oxide and zirconium oxide are especially preferred in that they can be prepared according to a sol-gel method capable of carrying out synthesis at low temperature and their precursors are easily available.

With respect to a coating method of an inorganic substance, reference is made to a known method, for example, a method described in "Application of Sol-Gel Method to Nanotechnology", published by CMC Shuppan (2005). For example, hydrolysis reaction of aluminum tri(sec-butoxide) is applied in forming an aluminum oxide coating, hydrolysis reaction of titanium tetraisopropoxide in forming a titanium oxide coating, and hydrolysis reaction of zirconium tetra-n-butoxide is applied in forming a zirconium oxide coating.

The thickness of the coating is not specifically limited, and is preferably from 5 to 30 nm in view of prevention of sedimentation at immunoassay.

[Organic Molecule Combining Fluorescent Substance-Containing Silica Nanoparticles with Molecule Labeling Agent]

The biosubstance labeling agent of the invention is one in which fluorescent substance-containing silica nanoparticles are combined with a molecule labeling agent through an organic molecule.

In order to combine fluorescent substance-containing silica nanoparticles with a molecule labeling agent through an organic molecule, an organic molecule capable of combining with the surface of the fluorescent substance-containing silica nanoparticles and of combining with the molecule labeling agent is used. Thus, the nanoparticles are modified with this organic molecule, and then the modified nanoparticles are combined with the molecule labeling agent, whereby the biosubstance labeling agent is obtained.

The combining types above are not specifically limited, and as the combining types, there are mentioned a covalent bond, an ionic bonding, a hydrogen bond, a coordination bond, and physical or chemical adsorption. In view of bonding stability, a bond with strong bonding force such as a covalent bond is preferred.

As an organic molecule, which is capable of combining with both fluorescent substance-containing silica nanoparticles and a molecule labeling substance, there is, for example, a silane coupling agent which is widely used in order to combining an inorganic substance with an organic substance.

This silane coupling agent is a compound which has at one end of the molecule an alkoxysilyl group providing a silanol group on hydrolysis and at the other end a functional group such as a carboxyl group, an amino group, an epoxy group, or an aldehyde group, and combines with an inorganic substance through the oxygen atom of the silanol group. Typical example s thereof include a mercaptopropyltriethoxysilane, glycidoxypropyltriethoxysilane and aminopropyltriethoxysilane.

Further, in order to prevent non-specific adsorption to a biosubstance, a silane coupling agent having a polyethylene glycol chain (for example, PEG-silane no.SiM 6492.7, produced by Gelest Co., Ltd.) can be used.

These silane coupling agents may be used as an admixture of two or more kinds thereof.

As a method of reacting fluorescent substance-containing silica nanoparticles with a silane coupling agent, a known method can be used. For example, fluorescent dye-containing silica nanoparticles are dispersed in pure water, added with aminopropyltriethoxysilane, and reacted at room temperature for 12 hours. After the reaction the reaction mixture is filtered off or centrifuged to obtain fluorescent substance-containing silica nanoparticles whose surface is modified by an aminopropyl group.

[Biosubstance Labeling Agent]

The biosubstance labeling agent in the invention can be obtained by combining the above fluorescent substance-containing silica nanoparticles with a molecule labeling agent through an organic molecule.

The biosubstance labeling agent in the invention can label a biosubstance by specifically combining and/or reacting a molecule labeling agent with the biosubstance as a target.

Typical examples of the biosubstance labeling agent include a compound having a nucleotide chain, a protein, an antibody and the like.

For example, the amino group of fluorescent substance-containing silica nanoparticles modified with aminopropyltriethoxysilane is reacted with the carboxyl group of an antibody, whereby the antibody is combined with quantum dot-containing silica nanoparticles through an amido group. As necessary, a condensation agent such as EDC (1-Ethyl-3-[3-Dimethylaminopropyl]carbodiimide hydrochloride, produced by Pierce Co., Ltd.) can be used.

Further, a linker compound can be used which has both a site capable of directly combining with fluorescent substance-containing silica nanoparticles modified with an organic molecule and a site capable of combining with a molecule labeling agent. For example, when sulfo-SMCC (Suifosuccinimidyl 4[N-maleimidomethyl]-cyclhexane-1-carboxylate, produced by Pierce Co., Ltd.) is used which has both a site selectively reacting with an amino group and a site selectively reacting with a mercapto group, the amino group of fluorescent substance-containing silica nanoparticles modified with aminopropyltriethoxysilane is combined with the mercapto group of the antibody, thereby obtaining fluorescent substance-containing silica nanoparticles combined with the antibody.

EXAMPLES

Next, the present invention will be explained, employing an example in which an organic dye tetramethylrhodamine is used as a fluorescent substance contained in silica nanoparticles and an example in which a quantum dot CdSe is used as a fluorescent substance contained in silica nanoparticles, but the invention is not specifically limited thereto. In the examples, "parts" and "%" represent parts by mass and % by mass, respectively, unless otherwise specified.

<<Fluorescent Substance-Containing Silica Nanoparticles>>

[Preparation of Silica Nanoparticles 1]
(Silica Nanoparticles 1: Tetramethylrhodamine-Containing Silica Nanoparticles)

Silica Nanoparticles 1 were prepared according to the following processes (1) through (4), referring to Patent Document 1, Process (1)

Two milligrams of tetramethylrhodamine (TAMRA-SE produced by Invitrogen Corporation) and 40 μl of tetraethoxysilane were mixed.

Process (2)

Four ml of ethanol and 1 ml of a 14% ammonia aqueous solution were mixed.

Process (3)

The mixed solution prepared in the Process (1) was added to the mixed solution prepared in the Process (2) while stirring at room temperature. The stirring was continued for 12 hours since addition of the former solution began.

Process (4)

The resulting reaction mixture was subjected to centrifugation at 10000 g for 60 minutes and the resulting supernatant was removed. The resulting precipitates were added with ethanol, re-dispersed in ethanol and then re-centrifuged. In the same way as above, washing with ethanol and washing with pure water each were carried out one time. Thus, Silica Nanoparticles 1 were obtained.

The Silica Nanoparticles 1 obtained above were observed employing an SEM. The average particle diameter and the coefficient of variation thereof were 110 nm and 12%, respectively.

[Preparation of Silica Nanoparticles 2]
(Silica Nanoparticles 2: CdSe-Containing Silica Nanoparticles)

Silica Nanoparticles 2 were prepared according to the following processes (1) through (4), referring to Patent Document 2.

Process (1)

Ten μl of a CdSe decane dispersion solution (Qdot 655, produced by Invitrogen Corporation) and 40 μl of tetraethoxysilane were mixed.

Process (2)

Four ml of ethanol and 1 ml of a 14% ammonia aqueous solution were mixed.

Process (3)

The mixed solution prepared in the Process (1) was added to the mixed solution prepared in the Process (2) while stirring at room temperature. The stirring was continued for 12 hours since addition of the former solution began.

Process (4)

The resulting reaction mixture was subjected to centrifugation at 10000 g for 60 minutes and the resulting supernatant was removed. The resulting precipitates were added with ethanol, re-dispersed in ethanol and then re-centrifuged. In the same way as above, washing with ethanol and washing with pure water each were carried out one time. Thus, Silica Nanoparticles 2 were obtained.

The Silica Nanoparticles 2 obtained above were observed employing an SEM. The average particle diameter and the coefficient of variation thereof were 130 nm and 13%, respectively.

[Preparation of Silica Nanoparticles 3]
(Silica Nanoparticles 3: Tetramethylrhodamine-Containing Silica Nanoparticles Coated With Titanium Oxide)

One ml of a water dispersion solution of silica nanoparticles 1 obtained in the above preparation of silica nanoparticles 1 was dispersed in 5 ml of pure water. The resulting dispersion solution was added with 10 μl of titanium tetraisopropoxide and 10 μl of a 14% ammonia aqueous solution and stirred at room temperature for 12 hours.

The resulting reaction mixture was subjected to centrifugation at 10000 g for 10 minutes and the resulting supernatant was removed. The resulting precipitates were added with ethanol, re-dispersed in ethanol and then re-centrifuged. In the same way a above, washing with ethanol and washing with pure water each were carried out one time. Thus, Silica Nanoparticles 3 were obtained.

[Preparation of Silica Nanoparticles 4]
(Silica Nanoparticles 4: Tetramethylrhodamine-Containing Silica Nanoparticles Coated With Zirconium Oxide)

The Silica Nanoparticles 4 were prepared in the same manner as in the Silica Nanoparticles 3, except that zirconium tetra-n-butoxide was used instead of titanium tetraisopropoxide.

[Preparation of Silica Nanoparticles 5]
(Silica Nanoparticles 5: CdSe-Containing Silica Nanoparticles Coated With Titanium Oxide)

The Silica Nanoparticles 5 were prepared in the same manner as in the Silica Nanoparticles 3, except that silica nanoparticles 2 obtained in the preparation of silica nanoparticles 2 were used instead of silica nanoparticles 1,

[Preparation of Silica Nanoparticles 6]
(Silica Nanoparticles 6: CdSe-Containing Silica Nanoparticles Coated With Aluminum Oxide)

The Silica Nanoparticles 6 were prepared in the same manner as in the Silica Nanoparticles 3, except that silica nanoparticles 2 obtained in the preparation of silica nanoparticles 2 were used instead of silica nanoparticles 1, and aluminum tri-sec-butoxide was used instead of titanium tetraisopropoxide.

[Preparation of Silica Nanoparticles 7]
(Silica Nanoparticles 7: CdSe-Containing Silica Nanoparticles Coated With Zinc Sulfide)

One ml of a water dispersion solution of silica nanoparticles 2 obtained in the preparation of the silica nanoparticles 2 was added with 100 μl of a 1 mol/liter zinc acetate aqueous solution and 100 μl of a 1 mol/liter sodium sulfide ethanol dispersion solution in that order and reacted at room temperature for 24 hours while stirring.

The resulting reaction mixture was subjected to centrifugation at 10000 g for 10 minutes and the resulting supernatant was removed. The resulting precipitates were added with ethanol, re-dispersed in ethanol and then re-centrifuged. In the same way as above, washing with ethanol and washing with pure water each were carried out one time. Thus, Silica Nanoparticles 7 were obtained.

[Preparation of Silica Nanoparticles 8]
(Silica Nanoparticles 8: Tetramethylrhodamine-Containing Silica Nanoparticles Coated With Silica)

The silica nanoparticles 1 obtained in the preparation of silica nanoparticles 1 were coated with silica employing tetraethoxysilane, referring to Patent Document 4. Thus, Silica Nanoparticles 8 were obtained,

[Preparation of Silica Nanoparticles 9]
(Silica Nanoparticles 9: CdSe-Containing Silica Nanoparticles Coated With Silica)

The Silica Nanoparticles 9 were prepared in the same manner as the Silica Nanoparticles 8, except that the water dispersion solution of Silica Nanoparticles 2 obtained in the preparation of Silica Nanoparticles 2 were used.

A 1 nM PBS (phosphate buffered saline) dispersion solution of each of the fluorescent substance-containing silica nanoparticles prepared above was prepared and allowed to stand at room temperature for one month. Thereafter, the dispersion solution of 1 ml was incorporated in a polypropylene tube with 1.5 ml content, and centrifuged at 12000 g for 20 minutes. Then, 0.9 ml of the supernatant solution were collected and the fluorescence intensity thereof was determined.

The leakage amount of the fluorescent substance from each of the tetramethylrhodamine-containing silica nanoparticles is expressed by a relative value of the fluorescence intensity of each of the tetramethylrhodamine-containing silica nanoparticles to the fluorescence intensity of silica nanoparticles 1 being set at 1.0, and the leakage amount of the fluorescent substance from each of the CdSe-containing silica nanoparticles by a relative value of the fluorescence intensity of each of the CdSe-containing silica nanoparticles to the fluorescence intensity of silica nanoparticles 2 being set at 1.0.

When the relative value is low, the amount of the fluorescent substance leaked to the solution is small, which exhibits superior storage stability. The results are shown in Tables 1 and 2.

TABLE 1

| | Silica nanoparticles No. | | | |
| --- | --- | --- | --- | --- |
| | 1 | 3 | 4 | 8 |
| Fluorescent Substance | | Tetramethylrhodamine (Orgainc Dye) | | |
| Coating | None | Titanium Oxide | Zirconium Oxide | Silica |
| Bulk Refractive Index of Coating | — | 2.58 | 2.20 | 1.45 |

TABLE 1-continued

| | Silica nanoparticles No. | | | |
|---|---|---|---|---|
| | 1 | 3 | 4 | 8 |
| Fluorescent Substance | | Tetramethylrhodamine (Orgainc Dye) | | |
| Leakage Amount of Fluorescent Substance | 1.0 | 0.1 | 0.2 | 1.2 |
| Remarks | Comparative | Inventive | Inventive | Comparative |

TABLE 2

| | Silica nanoparticles No. | | | | |
|---|---|---|---|---|---|
| | 2 | 5 | 6 | 7 | 9 |
| Fluorescent Substance | | | CdSe (Quantum Dot) | | |
| Coating | None | Titanium Oxide | Aluminum Oxide | Zinc sulfide | Silica |
| Bulk Refractive Index of Coating | — | 2.58 | 1.76 | 2.37 | 1.45 |
| Leakage Amount of Fluorescent Substance | 1.0 | 0.2 | 0.1 | 0.4 | 1.1 |
| Remarks | Comparative | Inventive | Inventive | Inventive | Comparative |

Tables 1 and 2 show that after allowed to stand for one month, fluorescent substance-containing silica nanoparticles coated with silica having a bulk refractive index of 1.45 according to a known technique have substantially the same fluorescent substance leakage amount as fluorescent substance-containing silica nanoparticles without a coating, and on the other hand, the fluorescent substance-containing silica nanoparticles coated with an inorganic material having a refractive index of from 1.60 to 4.00 greatly reduces the fluorescent substance leakage amount. It is considered that this reason is because the inorganic material having a refractive index of from 1.60 to 4.00 adsorbs the fluorescent substance to prevent the fluorescent substance from leaking out.

<<Biosubstance Labeling Agent>>

Molecule-Modified Silica Nanoparticles A, B and C were prepared from Silica Nanoparticles 3, Silica Nanoparticles 8 and Silica Nanoparticles 1, respectively. Then, Biosubstance Labeling Agent 1, 2 and 3 were prepared from Molecule-Modified Silica Nanoparticles A, Molecule-Modified Silica Nanoparticles B and Molecule-Modified Silica Nanoparticles C, respectively. Long term storage stability of the resulting Biosubstance Labeling Agents 1, 2 and 3 were evaluated.

[Preparation of Molecule-Modified Silica Nanoparticles A]
(Molecule-Modified Silica Nanoparticles A: Amino Group-modified Tetramethylrhodamine-Containing Silica Nanoparticles Coated with Titanium Oxide)

One milligram of tetramethylrhodamine-containing silica nanoparticles coated with titanium oxide obtained in the preparation of Silica Nanoparticles 3 was dispersed in 5 ml of pure water. The resulting dispersion solution was added with 100 μl of an aminopropyltriethoxysilane aqueous dispersion solution and reacted at room temperature for 12 hours while stirring.

The resulting reaction solution was centrifuged at 10000 g for 60 minutes, and the supernatant was removed. The resulting precipitates were dispersed in ethanol and re-centrifuged. Similarly, the resulting precipitates were washed employing ethanol and pure water.

Thus, amino group-modified tetramethylrhodamine-containing silica nanoparticles coated with titanium oxide were prepared, and subjected to FT-IR measurement. The absorption due to an amino group was observed and it was confirmed that the silica nanoparticles were modified with an amino group.

[Preparation of Molecule-Modified Silica Nanoparticles B]
(Molecule-Modified Silica Nanoparticles B: Amino Group-modified Tetramethylrhodamine-Containing Silica Nanoparticles Coated with Silica)

Tetramethylrhodamine-containing silica nanoparticles coated with silica obtained in the preparation of Silica Nanoparticles 8 was modified with an amino group in the same manner as in Molecule-Modified Silica Nanoparticles A.

The thus obtained amino group-modified tetramethylrhodamine-containing silica nanoparticles coated with silica were subjected to FT-IR measurement. The absorption due to an amino group was observed and it was confirmed that the silica nanoparticles were modified with an amino group.

[Preparation of Molecule-Modified Silica Nanoparticles C]
(Molecule-Modified Silica Nanoparticles C: Amino Group-modified Tetramethylrhodamine-Containing Silica Nanoparticles without a Coating)

Tetramethylrhodamine-containing silica nanoparticles without a coating obtained in the preparation of Silica Nanoparticles 1 was modified with an amino group in the same manner as in Molecule-Modified Silica Nanoparticles A.

The thus obtained amino group-modified tetramethylrhodamine-containing silica nanoparticles coated without a coating were subjected to FT-IR measurement. The absorption due to an amino group was observed and it was confirmed that the silica nanoparticles were modified with an amino group.

[Preparation of Biosubstance Labeling Agent 1]
(Biosubstance, Labeling Agent 1: Amino Group-Modified Tetramethylrhodamine-Containing Silica Nanoparticles Coated with Titanium Oxide-Antibody Conjugate)

A dispersion solution was prepared in which 0.5 mg of amino group-modified tetramethylrhodamine-containing silica nanoparticles coated with titanium oxide obtained in the preparation of Molecule-Modified Silica Nanoparticles A were dispersed in 0.5 nm of pure water. Then 0.1 ml of the dispersion solution was incorporated in 2 ml of DMSO, and added with sulfo-SMCC (produced by Pierce Co., Ltd.) and reacted for one hour. Subsequently, the excessive sulfo-SMCC was removed by centrifuge. Separately, anti-hCG antibodies were subjected to reduction treatment with 1 M dithiothreitol (DTT), and excessive DTT was removed through a gel filtration column.

The tetramethylrhodamine-containing silica nanoparticles subjected to sulfo-SMCC treatment and the anti-hCG antibody subjected to DTT treatment were mixed and reacted for one hour. Ten mM of mercaptoethanol were added to the resulting reaction mixture to terminate the reaction. Unreacted substances were removed through a gel filtration column. Thus, sulfonic acid group-containing tetramethylrhodamine-containing silica nanoparticles coated with titanium oxide (Biosubstance Labeling Agent 1), which were combined with the anti-hCG antibodies, were obtained.

[Preparation of Biosubstance Labeling Agent 2]
(Biosubstance Labeling Agent 2: Amino Group-modified Tetramethylrhodamine-containing Silica Nanoparticles Coated with Silica-antibody Conjugate)

The amino group-modified tetramethylrhodamine-containing silica nanoparticles coated with silica obtained in the preparation of Molecule-Modified Silica Nanoparticles B were treated in the same manner as in Biosubstance Labeling Agent 1. Thus, tetramethylrhodamine-containing silica nanoparticles coated with silica (Biosubstance Labeling Agent 2), which were combined with the anti-hCG antibodies, were obtained.

[Preparation of Biosubstance Labeling Agent 3]
(Biosubstance Labeling Agent 3: Amino Group-modified Tetramethylrhodamine-containing Silica Nanoparticles without a Coating-antibody Conjugate)

The amino group-modified tetramethylrhodamine-containing silica nanoparticles without a coating obtained in the preparation of Molecule-Modified Silica Nanoparticles C were treated in the same manner as in Biosubstance Labeling Agent 1. Thus, tetramethylrhodamine-containing silica nanoparticles without a coating (Biosubstance Labeling Agent 3), which were combined with the anti-hCG antibodies, were obtained.

Tetramethylrhodamine-containing silica nanoparticles coated with titanium oxide combined with anti-hCG antibodies obtained in the preparation of Biosubstance Labeling Agent 1 were added in a concentration of 0.1 nM to a phosphate buffered saline in a glass vial, and stored at 4° C. for one month. After storage, the resulting dispersion solution was subjected to immunoassay according to the following procedures.

1) Anti-hα subunit was fixed in the wells on a micro plate.
2) An antigen hGC was added to each of the wells varying its concentration.
3) After an excessive hCG was removed by washing, a dispersion solution of Biosubstance Labeling Agent 1 was added to each well.
4) Excessive Biosubstance Labeling Agent 1 was removed by washing.
5) Fluorescence intensity of each well was measured through a microplate reader.

The fluorescence intensity measured increased as the antigen concentration increased. That is, it has proved that the anti-hCG antibodies, which are combined with the tetramethylrhodamine-containing silica nanoparticles obtained in the invention, does not lose an antigen recognizing ability.

Similarly, after the tetramethylrhodamine-containing silica nanoparticles coated with silica (Biosubstance Labeling Agent 2) combined with the anti-hCG antibodies, and tetramethylrhodamine-containing silica nanoparticles without a coating (Biosubstance Labeling Agent 3) combined with the anti-hCG antibodies were stored at 4° C. for one month, the same immunoassay as above was applied thereto. The fluorescence intensity measured of each agent before the storage exhibited the same results as the Biosubstance Labeling Agent 1.

With respect to long term storage stability, a S/N ratio was determined. When the S/N ratio is high, it exhibits excellent long term storage stability.

The S/N ratio of fluorescene intensity S measured in the presence of 1 ng/ml of hCG antibodies and fluorescence intensity N measured in the absence of hCG antibodies is shown in Table 3.

TABLE 3

| | Biosubstance Labeling Agent No. | | |
|---|---|---|---|
| | 1 | 2 | 3 |
| Coating | Titanium Oxide | Silica | None |
| Bulk Refractive Index of Coating | 2.58 | 1.45 | — |
| S/N Ratio | 25 | 2.1 | 1.8 |
| Remarks | Inventive | Comparative | Comparative |

It has proved that the S/N ratio of inventive tetramethylrhodamine-containing silica nanoparticles coated with titanium oxide, which was obtained in the florescence immunoassay carried out after one month storage, is extremely high as compared with that of silica nanoparticles prepared according to a conventional technique. That is, the above results show that the present invention can provide a biosubstance labeling agent which excels in long term storage stability and enables high sensitive detection even after long term storage.

The invention claimed is:

1. Fluorescent nanoparticles comprising:
   silica nanoparticles;
   a fluorescent substance contained in the silica nanoparticles; and
   a coating on the silica nanoparticles wherein the coating is a material having a bulk refractive index of from 1.60 to 4.00.

2. The fluorescent nanoparticles as described in claim 1, wherein the material having a bulk refractive index of from 1.60 to 4.00 is a material having a bulk refractive index of from 1.76 to 2.58.

3. The fluorescent nanoparticles as described in claim 2, wherein the material having a bulk refractive index of from 1.76 to 2.58 is at least one selected from titanium oxide, zirconium oxide and aluminum oxide.

4. The fluorescent nanoparticles as described in claim 1, wherein the fluorescent substance is an organic dye.

5. The fluorescent nanoparticles as described in claim 1, wherein the fluorescent substance is a quantum dot.

6. A biosubstance labeling agent comprising a molecule labeling agent and fluorescent nanoparticles, wherein the molecule labeling agent combines with the fluorescent nanoparticles through an organic molecule, the fluorescent nanoparticles comprising:
   silica nanoparticles;
   a fluorescent substance contained in the silica nanoparticles; and
   a coating on the silica nanoparticles wherein the coating is a material having a bulk refractive index of from 1.60 to 4.00.

* * * * *